United States Patent [19]

Ullman

[11] 4,032,519

[45] June 28, 1977

[54] DIAZACYCLOBUTANES

[75] Inventor: Edwin F. Ullman, Atherton, Calif.

[73] Assignee: Syva Company, Palo Alto, Calif.

[22] Filed: May 1, 1975

[21] Appl. No.: 573,647

Related U.S. Application Data

[63] Continuation of Ser. No. 416,142, Nov. 15, 1973, abandoned, which is a continuation-in-part of Ser. No. 358,758, May 9, 1973, Pat. No. 3,953,444, which is a continuation-in-part of Ser. No. 196,724, Nov. 8, 1971, abandoned.

[52] U.S. Cl. .......................................... 260/239 A
[51] Int. Cl.² ..................................... C07D 229/00
[58] Field of Search ............................... 260/239 A

[56] References Cited

OTHER PUBLICATIONS

Singh et al., Tet. Letters, 1971, pp. 3935–3938.

Primary Examiner—Donald G. Daus
Assistant Examiner—Mark L. Berch
Attorney, Agent, or Firm—Townsend and Townsend

[57] ABSTRACT

Novel four-membered ring heterocycles are provided having two nitrogen atoms in the ring bonded to each other and being bonded to exocyclic oxygen atoms. Both reduced and oxidized forms of the diazacyclobutane are provided. Depending on the particular compounds, they find use as triplet quenchers, and as antioxidants in light susceptible systems.

3 Claims, No Drawings

DIAZACYCLOBUTANES

CROSS REFERENCE TO RELATED APPLICATIONS

This is a continuation of application Ser. No. 416,142 filed November 15, 1973, now abandoned, which application is a continuation-in-part of application Serial No. 358,758 now U.S. Pat. 3,953,444, filed May 9, 1973, which in turn is a continuation-in-part of application Ser. No. 196,724, filed Nov. 8, 1971, now abandoned.

BACKGROUND OF THE INVENTION

1. Field of the Invention

In photochemical reactions, the course of the reaction can be affected by the excited state from which the product is formed. The excited state is determined initially by the energy absorbed by the molecule, but the initial state may be changed by interaction with the molecule's environment. Singlet and triplet states are the common photochemical excited states, which may be achieved by either direct absorption of energy or by use of a sensitizer.

The reaction product can depend on the excited state from which the reaction product is derived, not only as to isomer, but also in some cases as to structure, such as cyclizations. Therefore, where the possibility exists for two different products to be obtained, depending on the nature of the excited state, a quencher may be employed to dissipate the energy of one of the excited states in a manner which does not result in product formation.

Quenchers also find use in the study of photochemical reactions. In order to ascertain whether a particular product is formed through a triplet or singlet state, a quencher may be employed which will prevent the reaction from going through a triplet state. In this manner, if the reaction proceeds in the presence of the quencher, assuming the quencher has the appropriate triplet energy value ($E_T$), then the triplet state of the reactant must be very short lived or the reaction must proceed by means of a singlet state. The lower the triplet energy value for the molecule which is undergoing reaction, the lower the triplet energy value required for the quencher. Therefore, quenchers with low triplet energy values can be quite valuable in being able to quench reactions which occur at relatively low energy values. However, the quencher must not absorb the exciting light as this would inhibit the photochemical reaction. Ideal quenchers, therefore, have high singlet energies and low triplet energies.

2. Description of the Prior Art

A list of quenchers may be found in the 1971 J. T. Baker catalog. The description of the use of quenchers may be found in Turro, "Molecular Photochemistry", Benjamin, New York, 1967. The reaction of 1,2-bis(-hydroxylamino) tetramethylethane is reported to give a 1-oxylaziridine in Luckhurst et al., Tetrahedron Letters, 675 (1971).

SUMMARY OF THE INVENTION

Novel 1,2-diazacyclobutanes having nitrogen bonded to exocyclic oxygens are provided by oxidation of 1,2-bis(hydroxylamines). The products have a wide range of solubilities, and the dioxide compound is a triplet quencher having a low triplet energy value. The dioxide compound also acts as an antioxidant and inhibitor of photooxidation.

DESCRIPTION OF THE SPECIFIC EMBODIMENTS 1,2-diazacyclobutanes, wherein the nitrogen atoms are bonded to exocyclic oxygen are provided having at least 6 carbon atoms and not more then about 36 carbon atoms, usually from about 6 to 20 carbon atoms, and more usually from about 6 to 12 carbon atoms. The substituents at the 3 and 4 positions are hydrocarbon or substituted hydrocarbon. The substituents at the 3 and 4 position are usually aliphatically saturated or unsaturated hydrocarbon, usually having not more than one site of aliphatic unsaturation, and may be aliphatic, alicyclic, aromatic, or combinations thereof. Other than to the annular atoms, the annular nitrogen atoms are bonded solely to oxygen, either hydroxyl or oxide oxygen. The oxide compound is in a higher oxidation state than the hydroxyl compound and may be prepared from the appropriate acyclic bis-(hydroxylamino) compound, either directly without intermediance of the cyclic dihydroxy compound, or from the dihydroxy compound.

The first compound to be considered will be the dioxide compound, which, for the most part, will have the following formula:

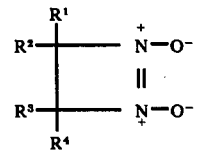

wherein $R^1$, $R^2$, $R^3$ and $R^4$ are the same or different and are mono-valent organic radicals, hydrocarbon or substituted hydrocarbon radicals, either aliphatic, alicyclic, aromatic, or combinations thereof. Conveniently, the molecule will have a line of symmetry, with $R^1$ and $R^2$ being the same as $R^3$ and $R^4$ respectively.

Each of $R^{1-4}$ will usually be of from 1–12 carbon atoms, more usually of from 1–8 carbon atoms, and normally of from 1–6 carbon atoms. While $R^{1-4}$ may be aliphatic, aromatic, alicyclic or combinations thereof, $R^{1-4}$ are preferably aliphatic, having from 0–1 aliphatic site of unsaturation, e.g., ethylenic.

Illustrative hydrocarbon groups include methyl, ethyl, propyl, cyclopentyl, cyclohexyl, benzyl, tolyl, phenyl, allyl, crotonyl, propargyl, etc.

The subject compounds of the above formula are (1,2-diazetine-1)-1,2-dioxides. Illustrative compounds include 3,3,4,4-tetramethyl-(1,2-diazetine-1)-1,2-dioxide, 3,4-dimethyl-3,4-ditolyl-(1,2-diazetine-1)-1,2-dioxide, 3,4-dimethyl-3,4-dipropyl-(1,2-diazetine-1)-1,2-dioxide; 3,3,4,4-tetraphenyl-(1,2-diazetine-1)-1,2-dioxide, 3,3-dimethyl-4,4-diphenyl-(1,2-diazetine-1)-1,2-dioxide, etc. oxidizing agent, such as lead dioxide, sodium hypobromite or sodium periodate. Alternatively, the bis(hydroxylamine) may be oxidized directly to the dioxide compound with sodium hypobromite.

The subject compounds are soluble in a wide range of solvents, varying from non-polar hydrocarbons to water, halohydrocarbons, polar ketones, alcohols, and nitriles. Therefore, these compounds can be used in a wide variety of media. The compounds are stable on storage under mild conditions.

The dioxide compound finds particular use as a triplet quencher, where quenching of either high or low energy triplets is desired. Furthermore, because of the wide range of solubility, the dioxide compound is particularly versatile as to the choice of solvent. It is high singlet energy and low triplet energy make it an especially useful quencher of triplet state of molecules having relatively high energy singlet states. In using the compound as a quencher, one merely adds the compound to the reaction medium and irradiates the medium with light of wavelength greater than 300nm. Useful concentrations of the quenchers are normally less than 0.1 molar and may be as low as $10^{-6}$ molar, depending on the particular compound in the triplet state being quenched.

The dioxide compounds also find use as antioxidants and photooxidation inhibitors, in oxidation susceptible media. By combining the dioxide with the oxidation susceptible substrate, such as polymers, oils, paints, etc., in amounts usually ranging from 0.001 to 0.5 weight percent, substantial protection of the substrate can be achieved. The dioxide may also be used to inhibit photoinitiated polymerizations in amounts of $10^{-4}$ to 0.5 weight percent.

The following examples are offered by way of illustration and not by way of limitation.

(All temperatures are centigrade unless otherwise indicated).

EXAMPLE A a. A mixture of 6 N sodium hydroxide (675 ml.) and 356 g. of 2-nitropropane (4 moles) as stirred and cooled while 320 g. of bromine (2 moles) was added dropwise. Then ethanol was added and the solution refluxed gently (3 hours) before being mixed with ice water (1.5 liters). The crystalline product was washed thoroughly with 50% ethanol: yield 280 g., m.p. 213°–215° C. (lit. 215°).

b. 2,3-dimethyl-2,3-dinitrobutane (175g., 1 mole) was stirred in suspension in a solution of ammonium chloride (100g., 1.9 moles) in 50% aqueous ethanol (2 liters) and kept below 15° while zinc dust (400g., 6.2 moles) was added during 3 hours. The reaction mixture was allowed to come to room temperature and stirred overnight. After filtration, the combined filtrate and washings were acidified to pH 2 (150 ml. hydrochloric acid) and evaporated under reduced pressure to a viscous state. Anhydrous potassium carbonate (1 kilogram) was stirred in while cooling, and the resulting powder extracted continuously with chloroform (2.5 liters) overnight. The chloroform extract was dried over anhydrous sodium carbonate, and evaporated to a viscous oil. Petroleum ether was added to promote crystallization of the product (40g.), m.p. 162°–163° (lit. 157°–159°).

c. Preparation of the above dinitro compounds is reported by L. W. Seigle and H. B. Hass in Journal Organic Chemistry, Volume 5 (1940), page 100. In this work the authors report a method for the synthesis of variety of dinitro compounds including those in which $R^1$, $R^2$, $R^3$ and $R^4$ are alkyl groups, aryl groups and asymmetrical combinations such as the following:

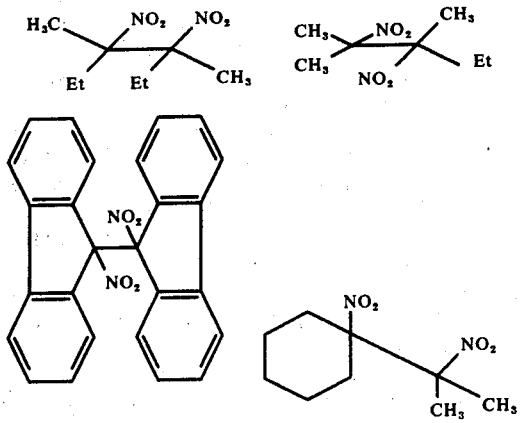

In those situations where a product is desired in which $R^1$ is the same as $R^3$ and $R^2$ is the same as $R^4$, a synthesis in accordance with Sayre, J. Am. Chem. Soc., 77, 6689 (1955) is preferably followed.

EXAMPLE I.

3,3,4,4-Tetramethyl-1,2-diazetine-1,2-dioxide

A. To a stirred solution of N,N'-dihydroxy 2,3-dimethyl-2,3-diaminobutane (5 g.) in water (250 ml.), bromine (4 ml.) was added dropwise at room temperature. The addition of bromine took 30 min. The reaction mixture was stirred for an additional period of 30 min. and the product extracted with chloroform. The organic extract was washed with 10% aqueous sodium sulfite to remove excess bromine, and then with a saturated solution of 10% sodium bicarbonate followed by water. The chloroform layer was dried (MgSO$_4$) and removal of the solvent in vacuo afforded white crystals of the product (2.9 g., 60%). Further crystallization from methanol afforded colorless needles; m.p. 190°–2° (d); ir (CHCl$_3$) 2410, 1555, 1460, 1440, 1385, 1140, 1015, 910 and 625 cm$^{-1}$; nmr (CDCl$_3$) δ1.64 (s); UV (CH$_3$CN) 254 nm (ε 10,500).

B. The product could also be obtained by oxidation of the dihydroxylamino precursor with sodium periodate. Thus, N,N'-dihydroxy 2,3-dimethyl-2,3-diaminobutane (1.5 g.) in water (50 ml.) was stirred for 30 min. with aqueous sodium periodate (4.5 g. in ca. 100 ml. water). The product precipitated out and was extracted with chloroform. The chloroform extract was washed with water, dried (MgSO$_4$), and evaporated to give the product (800 mg., 65°) T.L.C. (silica, CHCl$_3$/MeOH:4/1) one spot, R$_f$ 0.8).

EXAMPLE II

Mixture of 3,3,4,4-Tetramethyl-1,2-diazetine-1,2-dioxide (1) and N,N'-dihydroxy 3,3,4,4-tetramethyl-1,2-diazetidine (2)

To a stirred aqueous solution of N,N'-dihydroxy 2,3-dimethyl-2,3-diaminobutane (6 g. in 175 ml. water) was added slowly (in a ca. 1 ml. aliquots) a saturated aqueous solution of socium periodate (ca. 25 ml.) until the reaction mixture turned brownish orange. Sodium periodate addition was stopped and excess periodate destroyed with aqueous sodium sulfite (10%). The product was extracted with chloroform, washed with saturated aqueous sodium chloride and dried. Removal of the solvent gave a mixture of the same products as a white solid. Vacuum (0.05 mm.) sublimation at room temperature gave pale yellow microcrystals of (2) (1.3 g.) which, when resublimed, afforded white crystals, mp 59°–61°; ir (CCl$_4$) 3620 (sharp), 3100–3500, 2930, 1675, 1470, 1435, 1380, 1370, 1268, 1068, 940, and 715 cm$^{-1}$; nmr (CDCl$_3$) δ1.94 (s,12H, CH$_3$ groups) and 9.14 (br s, 2H, OH protons, absent when the sample was washed with D$_2$O); R$_f$ (silica/ether)=0.7. Anal.

Calcd for $C_6H_{14}N_2O_2$: C, 49.30; H, 9.65; N, 19.17; Found: C, 49.59; H, 9.57; N, 18.89.

The residue was found to be pure compound (1) (nmr and tlc analysis) (1.2 g.). The relative ratio of (1) and (2), as determined by nmr of the crude mixture was 35:65 respectively.

EXAMPLE III

N,N'-Dihydroxy 3,3,4,4-tetramethyl-1,2-diazetidine.

A solution of N,N'-dihydroxy 2,3-dimethyl-2,3-diaminobutane I (6 g.) in water (500 ml.) was added dropwise, over a period of 2 hours, to a suspension of manganese dioxide (45 g.) in water (150 ml.) at 75°-80° C. The reaction mixture was further stirred at 75°-80° for 6 hours and refluxed for 2 hours. The reaction mixture was cooled to room temperature and filtered. The filtrate was saturated with solid ammonium chloride and extracted with chloroform. Removal of the solvent from the dried extract furnished the product, as white crystals (3.6 g., 60%), which was further purified by sublimation.

To demonstrate the effectiveness of the subject dioxide compounds as triplet quenchers, the following reactions were carried out.

Two aliquots of 1:1 solution of methanol and tert.-butanol were prepared having $5.7 \times 10^{-3}$ molar concentrations of ditoluoyl. In one of the solutions, the compound of Example I was introduced at a concentration of $5.41 \times 10^{-3}$ molar. The two solutions were irradiated for about 57 minutes with UV light having a wavelength equal to or greater than about 390 m$\mu$. While the sample without the compound of Example I underwent a significant change in spectrum having an isosbestic point at 375 m$\mu$, there was substantially no change in the spectrum of the tube having the compound of Example I.

Under analogous conditions, the compound of Example I was found to also inhibit the addition of oxygen to anthracene, when anthracene was irradiated with light in the presence of oxygen, under conditions where in the absence of the quencher, oxygen would add to anthracene.

Finally, the Ullman color test, described in Weissberqer, Techniques of Organic Chemistry, Volume 14, Interscience Publishers, New York (1969) indicated that the triplet energy value ws equal to or less than about 43 kcal. This value is extremely low as compared to most available quenchers.

The compounds of the subject invention are quite versatile having a variety of utilities. The dioxide compound with its wide range of solubilities and low triplet energy value is extremely important as a triplet quencher. Furthermore, the dioxide compound inhibits photoinduced oxidation and polymerization in photosusceptible media.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A compound of the formula:

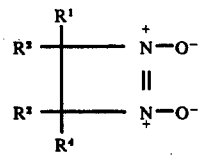

wherein $R^{1-4}$ are the same or different and are monovalent aliphatic hydrocarbon radicals of from 1 to 12 carbon atoms of from 0 to 1 site of ethylenic unsaturation.

2. A compound according to claim 1, wherein said aliphatic hydrocarbon radicals are of from 1 to 6 carbon atoms.

3. 3,3,4,4-tetramethyl-1,2-diazetine-1,2-dioxide.

* * * * *

UNITED STATES PATENT AND TRADEMARK OFFICE
CERTIFICATE OF CORRECTION

PATENT NO. : 4,032,519
DATED : June 28, 1977
INVENTOR(S) : EDWIN F. ULLMAN

It is certified that error appears in the above-identified patent and that said Letters Patent are hereby corrected as shown below:

Insert as co-inventor: David G.B. Boocock, Ontario, Canada.

Signed and Sealed this

Twenty-fourth Day of April 1979

[SEAL]

Attest:

RUTH C. MASON
Attesting Officer

DONALD W. BANNER
Commissioner of Patents and Trademarks